US006325995B1

(12) United States Patent
El-Nokaly et al.

(10) Patent No.: US 6,325,995 B1
(45) Date of Patent: Dec. 4, 2001

(54) LIPSTICKS COMPOSITIONS CONTAINING ASSOCIATION STRUCTURES

(75) Inventors: Magda El-Nokaly, Cincinnati, OH (US); David William Walling, Parkton, MD (US); Michael L. Vatter, Okeana, OH (US); Neil Campbell Leatherbury, Baltimore, MD (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 08/115,093

(22) Filed: Sep. 7, 1993

Related U.S. Application Data

(63) Continuation-in-part of application No. 08/066,351, filed on May 21, 1993, which is a continuation-in-part of application No. 07/947,692, filed on Sep. 21, 1992.

(51) Int. Cl.[7] .......................... A61K 7/021; A61K 7/025; A61K 9/127
(52) U.S. Cl. ................................ 424/64; 424/63; 424/450
(58) Field of Search ................................ 424/63, 64, 450

(56) References Cited

U.S. PATENT DOCUMENTS

| 3,642,980 | 2/1972 | Lachampt | 424/64 |
|---|---|---|---|
| 3,957,969 | 5/1976 | Fujiyama et al. | 424/64 |
| 3,957,971 | 5/1993 | Oleniacz | 424/70 |
| 4,301,023 | 11/1981 | Schuberth et al. | 252/299.7 |
| 4,600,526 | 7/1986 | Gallot et al. | 252/299.01 |
| 4,760,096 | 7/1988 | Sakai et al. | 514/847 |
| 4,767,625 | 8/1988 | Mitsumo et al. | 424/95 |
| 4,999,348 | 3/1991 | Cioca et al. | 514/171 |
| 5,034,216 | 7/1991 | Barone et al. | 424/63 |
| 5,085,856 | 2/1992 | Dunphy et al. | 424/64 |

(List continued on next page.)

FOREIGN PATENT DOCUMENTS

| 1008876 | 4/1977 | (CA) . | |
|---|---|---|---|
| 0217105 | 4/1987 | (EP) . | |
| 04519149 | 10/1991 | (EP) . | |
| 0474270 | 3/1992 | (EP) . | |
| 0534823 | 3/1993 | (EP) . | |
| 0534823B1 | 3/1993 | (EP) | A61K/7/00 |
| 0522624 | 1/1993 | (EP) | A61K/7/027 |
| 0 105 657 | 9/1983 | (EP) | A61K/7/48 |
| 0 512270 | 11/1992 | (EP) | A61K/7/48 |
| 0524892 | 1/1993 | (EP) | A61K/7/48 |
| 2614-787-A | 11/1988 | (FR) | A61K/7/48 |
| 2633-515-A | 1/1990 | (FR) | A61K/7/48 |
| 54049337 | 4/1979 | (JP) | A61K/7/02 |
| 6089832-A | 7/1981 | (JP) | B01J/13/00 |
| 58183609 | 10/1983 | (JP) | A61K/7/02 |
| 6 0153 938 A | 8/1985 | (JP) | A23L/1/03 |
| 61083110 | 4/1986 | (JP) | A61K/7/025 |
| 62-205187 | 9/1987 | (JP) | A61K/7/00 |
| 62-205188 | 9/1987 | (JP) | A61K/7/00 |
| 01233206 | 9/1989 | (JP) . | |
| 01246209 | 10/1989 | (JP) | A61K/7/00 |
| 02117987-A | 5/1990 | (JP) | A61K/7/00 |
| 02178209 | 7/1990 | (JP) | A61K/7/00 |
| 2191-208-A | 7/1990 | (JP) . | |
| 2200-607-A | 8/1990 | (JP) . | |
| 2200-608-A | 8/1990 | (JP) . | |
| 02-306910 | 12/1990 | (JP) | A61K/7/25 |
| 03034907-A | 2/1991 | (JP) | A61K/7/00 |
| 3074-313-A | 3/1991 | (JP) | A61K/47/12 |
| 03240715 | 10/1991 | (JP) | A61K/7/00 |
| 3240-714-A | 10/1991 | (JP) . | |
| 04015289-A | 1/1992 | (JP) | C09K/19/36 |
| 04108718-A | 4/1992 | (JP) | A61K/7/025 |

(List continued on next page.)

OTHER PUBLICATIONS

Bevacqua et al., "Liquid Crystals in Multiple Emulsions", Cosmetics & Toiletries, vol. 106, pp. 55–56, May 1990.
Cloca et al., "Liquid Crystals and Cosmetic Applications" Cosmetics & Toiletries vol. 105 57–62 May, 1990.
Dahms, G. "Rheology of Cosmetic Water–In–Oil Formulations" Seifen Oele Fette Wachse, 117(4), 145–50, 1991. (Eng. Abstract).
El–Nokaly et al. "Lyotropic Liquid Crystals from Lecithin, Water, Polyethylene Glycol" J. Colloid and Interface Sci, 98(1). Mar. 1984.
El–Nokaly et al., "The structure of Lamellar Lyotropic Liquid Crystals From Lecithin and Alkane–Diols", Journal of Colloid Interface Science, vol. 84, p. 228, 1981.
El–Nokaly et al., "Non aqueous Lytropic Liquid Crystals of Lecithin and Oligomers of Poyethylene Glycols", Liquid Crystals and Ordered Fluids, vol. 14 p. 441, 1981.
Luedthe et al., "Guidelines for the Product Development, Production and Quality Assurance of Toilet Articles: Part 2 Special Product Development" [Review of formulae and process development of cosmetics for the lips] Seifen Oele Fette Wachse vol. 115, #15, pp. 521–533, 1989. [Formulae for moisturizing lipsticks are given.].
Moucharafieh, N., "A First Comparison Between Aqueous and Non Aqueous Lyotropic Liquid Crystalline Systems", Chemistry Department UMR, Rolla, Mo. Submitted for Publication: Feb. 26, 1979.
Nagai, M. (Pola), "Research of Liquid Crystal and Emulsificaiton for Cosmetics", Shikizai, vol. 58, No. 6, pp. 350–355, 1985.

*Primary Examiner*—Thurman K. Page
*Assistant Examiner*—S. Howard
(74) *Attorney, Agent, or Firm*—John M. Howell; George W. Allen; Dara M. Kendall

(57) ABSTRACT

The present invention relates to lipstick compositions which comprise thermodynamically association structures, preferably lamellar liquid crystals and/or reverse hexagonal liquid crystals, which are used to deliver polar solvent/moisturizers through a non-polar (lipophilic) medium. The association structures consist essentially of from about 3% to about 96%, by weight, of polar solvent (e.g. glycerine) and from about 4% to about 97% of surfactant having a Krafft point at or below about ambient temperature.

31 Claims, No Drawings

U.S. PATENT DOCUMENTS

| | | | |
|---|---|---|---|
| 5,156,766 | 10/1992 | Behan et al. | 252/312 |
| 5,157,046 | 10/1992 | Van Wauwe et al. | 514/397 |
| 5,215,757 | 6/1993 | El-Nokaly | 424/488 |

FOREIGN PATENT DOCUMENTS

| | | | |
|---|---|---|---|
| 04108718 | 4/1992 | (JP) | . |
| 4243806 | 8/1992 | (JP) | A61K/7/00 |
| 4338311 | 11/1992 | (JP) | A61K/7/00 |
| WO 91/13125 | 2/1991 | (WO) | C09K/19/52 |

OTHER PUBLICATIONS

Schambil, F., "New Forms of Aggregation of Surfactants for Cosmetic and Pharmaceutical use (liquid crystals, vesicles and micro emulsions)", Aerosol Cosmet., 7(37) pp. 12–16, 1985.

LIPSTICKS COMPOSITIONS CONTAINING ASSOCIATION STRUCTURES

This is a continuation-in-part of application Ser. No. 08/066,351, filed on May 21, 1993, which is a continuation-in-part of application Ser. No. 07/947,692 filed on Sep. 21, 1992.

FIELD OF THE INVENTION

This invention relates to lipstick compositions which comprise thermodynamically stable association structures which are used to deliver polar moisturizing agents through a nonpolar (lipophilic) matrix. The invention provides for a lipstick with optimum stability of the polar moisturizing agents, while also providing moisturizing benefits to the lips.

BACKGROUND OF THE INVENTION

Lipsticks are primarily composed of hydrocarbon waxes, esters of fatty acids or alcohols and oils. Water and other polar solvents, such as glycerine and propylene glycol, which can provide moisturization benefits are not soluble in this lipophilic matrix. As a result, various emulsifiers have been added to lipsticks in an attempt to emulsify the moisturizers/polar solvents. There has been partial success in this area by utilizing the emulsifiers and moisturizers/polar solvents at low concentrations. However, the moisturizers/polar solvents may separate from the lipstick causing it to look wet and messy. This is unacceptable to the consumer.

Thus a need exists to provide a lipstick which binds thermodynamically the moisturizers/polar solvents (discontinuous phase) and deliver them in a predominately nonpolar lipophilic matrix (continuous phase). Further, there is a need to provide a means of thermodynamically binding the moisturizers/polar solvents in such a way which will allow incorporation of high levels of the moisturizing agents while exhibiting overall excellent stability and providing good feel properties.

It has been discovered that association structures consisting essentially of a surfactant or mixture of surfactants having a Krafft point at or below about ambient temperature (about 20° C.) and a moisturizer/polar solvent can thermodynamically bind the moisturizer/polar solvent and homogeneously absorb in the lipophilic matrix while providing good feel and a means of delivering the moisturizing agents to the lips. Thus, the association structures of this invention can be used to deliver the moisturizers/polar solvents without syneresis, the separation of the hydrophilic materials. It has been discovered that upon application to the lips the preferred association structures of the present invention form a film on the lips which can act as a reservoir for the moisturizer/polar solvent.

It is particularly desirable that the lipsticks comprising said association structures be made from ingredients that are presently used and approved for use in edible product applications and for applying to the skin. It is an object of this invention to provide a delivery system for moisturizers/polar solvents through the nonpolar matrix of the lipstick while providing good feel. It is another object of this invention to provide a lipstick composition which can be easily molded yet contain high levels of moisturizers.

Sweating, the excretion of oil on the surface of a lipstick, is a common problem. Lipsticks are a complex mixture of solid, semi-solid and liquid lipids. Wax networks suspend the oils present in the lipstick. Sweating occurs due to the inferior oil-binding capacity of the wax network and/or to a high oil content causing supersaturation. The phenomenon can occur in any climate or temperature; although, it is more apt to occur in sub-tropical and tropical climates.

In most cases, castor oil has been identified as the excreted oil. A major ingredient of most lipstick formulations, castor oil can generally comprise up to forty percent of lipsticks. The high percentage of castor oil is primarily due to its unique properties as a wetting agent for pigments. Monodispersions of pigments are commonly made in slurries comprising from about 30% to about 40% pigments and from about 60% to about 70% castor oil.

It is an object of this invention to provide a preferred lipstick composition of the present invention which is substantially free of castor oil. It is an object that the lipstick be castor oil sweat resistant or castor oil sweat free. An added benefit to removing the castor oil is the removal of the castor oil odor.

It has been discovered that the association structures, preferably lamellar liquid crystals (neat phase), can be used to deliver moisturizing agents in lipsticks which are substantially free of castor oil. It has been found that removal of the castor oil, typically present in the range of from about 30% to about 50% of the lipstick compositions, allows for optimization of emollients; thus, providing for a more consumer acceptable feel, such as less tackiness, and moisturizing benefits by utilizing more lubricious emollients.

All percentages and ratios stated herein are by weight unless otherwise indicated.

SUMMARY OF THE INVENTION

The present invention relates to lipstick compositions which comprise association structures which are used to deliver moisturizing agents/polar solvents into a non-polar/lipophilic medium in a thermodynamically stable way. A method of making the lipstick is also disclosed.

The lipstick compositions comprise:
(a) from about 5% to about 90%, by weight, of wax;
(b) from about 1% to about 90%, by weight, of an emollient component comprising from 0% to about 100%, by weight, of oil liquid at ambient temperature;
(c) from about 0.1 to about 80%, by weight, of an association structure consisting essentially of:
  (1) from about 3% to about 96%, by weight, of polar solvent; and
  (2) from about 4% to about 97% by weight, of surfactant having a Krafft point at or below about ambient temperature; and
(d) from 0% to about 35%, on an anhydrous basis, of color;

Preferred lipstick compositions are substantially free of castor oil, contain a coupling agent, and/or have compatible solubilities for wax and oil components. These lipstick compositions provide moisturizing, long wear and good feel properties.

Without intending to necessarily limit the scope of the invention, it is believed that the association structures adsorb onto solid/liquid, or liquid/liquid interfaces in heterogeneous systems such as lipsticks and other cosmetic sticks. An association structure, preferably a liquid crystalline lamellar phase, forms in the continuous phase. These association structures are able to flow under shear and act as lubricants between the different components of the heterogeneous systems such as the solids and other materials in the product. They also stabilize the actives by entrapping the liquid, solids particles or droplets in their matrix and preventing them from flocculating and further coalescing.

DETAILED DESCRIPTION OF THE INVENTION

Definition

As used herein, the term "solid material" refers to any solid lipstick ingredient capable of adsorbing the association structures. Solids include waxes, solid fats, waxy emulsifiers or pigments commonly used in lipsticks.

As used herein, "color(s)" includes pigments, dyes, colors, lakes, and pearl. Colors are measured on an anhydrous weight basis.

As used herein, the term "lecithin" refers to a material which is a phosphatide. Naturally occurring or synthetic phosphatides can be used. Phosphatidylcholine or lecithin is a glycerine esterified with a choline ester of phosphoric acid and two fatty acids, usually a long chain saturated or unsaturated fatty acid, having 16–20 carbons and up to 4 double bonds. Other phosphatides capable of forming association structures, preferably lamellar or hexagonal liquid crystals, can be used in place of the lecithin or in combination with it. Other phosphatides are glycerol esters with two fatty acids as in the lecithin, but the choline is replaced by ethanolamine (a cephalin), or serine (a-aminopropanoic acid; phosphatidyl serine) or an inositol (phosphatidyl inositol).

As used herein, the term "surfactant" refers to a low molecular weight or monomer non-polymeric organic compound amphiphilic in nature, i.e., it has hydrophilic and hydrophobic groups and exhibits a marked tendency to adsorb on a surface or interface and lower the surface tension. Surfactants or emulsifiers are divided into nonionic (no charge), anionic (negative charge), cationic (positive charge) and amphoteric (both charges) based on whether or not they ionize in aqueous media. Surfactants are monomers and are derived from natural oils and fats and crude oils. The term "surfactant" as used herein refers to mixtures of surfactants as well as a single organic compound.

As used herein, "polar solvent" means a polar material capable of forming an association structure with a surfactant. Some examples of polar solvents include glycerine, panthenol (preferably panthenol mixed with glycerine or alcohol), propylene glycol, butylene glycol, water, alcohols, alkanediols, polyethylene glycols, sorbiton, maltilal and mixtures thereof.

As used herein the term "comprising" means that the composition can contain other ingredients which are compatible with the composition and which preferably do not substantially disrupt the association structure lipstick compositions of the present invention. The term encompasses the terms "consisting of" and "consisting essentially of".

Essential Components

Association Structures

As used herein "association structure" refers to reverse micelle and lyotropic liquid crystal structures which are formed by the mixture of a surfactant or mixture of surfactants and a polar solvent or mixture of polar solvents at ambient temperature. The liquid crystalline state is an intermediate state between the solid and liquid states. It is often called a mesomorphic state. The association structures of the present invention are thermodynamically stable. They are distinguishable from gels or emulsions which have the polar solvent separate when subjected to ultracentrafugation. Separation means that generally at least 50%, preferably at least 80% and more preferably at least 99%, of the polar solvent separates. Further, they are distinguished in that the lyotropic liquid crystalline state can be identified by one of ordinary skill in the art by known means such as transmission electron microscopy (TEM) or birefringence under polarized light and x-ray diffraction.

In the literature, association structures are also referred to as anisotropic fluids or in the case of the cubic phase as isotropic fluids, a fourth state of matter, liquid crystals, aggregates, or mesophases. These terms are used interchangeably. Association structures or aggregates are generally disclosed in the reference *Lyotropic Liquid Crystals* Stig Friberg (Ed.), American Chemical Society, Washington, D.C., 1976, pp 13–27 which is herein incorporated by reference.

The association structures of the present invention, are prepared by mixing a surfactant having a Krafft point at or below about ambient temperature with a sufficient amount of a polar solvent to form the desired association structure. Each surfactant has a temperature and concentration range in which the association structure will exist based on the surfactant's chemical structure, the type of solvent being used, and the presence of any impurities. The liquid crystalline phase flows under shear and is characterized by a viscosity that is significantly different from the viscosity of its isotropic solution phase. Rigid gels do not flow under shear like liquid crystals. Also, when viewed with a polarized light microscope, liquid crystals show identifiable birefringence, as, for example, planar lamellar birefringence, whereas when isotropic solutions and rigid gels are viewed under polarized light, both show dark fields. Exceptions to this method of detection can occur for example with the cubic phases which can not be dectected by a polarized light microscope but can be detected by x-ray diffraction. Other methods of detection comonly used by ones of ordinary skill in the art are given infra.

Adding a gel or emulsion of a surfactant with a polar solvent to a fat, oil, wax or other hydrophobic medium often leads to unacceptable results because they are not thermodynamically stable. Emulsifying the oil/water and surfactant does not provide a thermodynamically stable system. The polar solvent would be expected to separate during storage or use and with changes in temperature. Adding the association structures of the present invention to the same system provides a system which is stable on storage because the association structure of the surfactant and polar solvent are thermodynamically stable and adsorb on the wax. The association structures can tolerate wide changes of temperatures, e.g. from ambient temperature to about 100° C. The polar solvent is bound within multilayers and does not separate, even when ultracentrifuged.

Micelles are large polymolecular aggregates in solutions. Normal micelles predominate in surfactant solutions above the critical micelle concentration which occurs at the Krafft temperature. The lipophilic groups accumulate in the liquid-like inner part of the aggregates. The hydrophilic groups are directed out towards the water. "Inverted" micelles in a hydrocarbon environment have their polar groups piled up in the inner part of the micelles. These reverse micelles can aggregate to form spherical, elongated, cylindrical, filament structures or mixtures thereof which can network in the hydrocarbon environment. The term "reverse micelles", as used herein, refers to these aggregates of reversed micelles which are the spherical, elongated, cylindrical, or filament structures and/or mixtures thereof. The spherical are liquid-like and as they become larger, i. e., elongated, they are gel-like.

One type of association structure, the liquid crystals, are a fourth state of matter. They exist between the boundaries of the solid phase and the isotropic liquid phase (i.e. an intermediate between the three dimensionally ordered crystalline state and the disordered dissolved state). In this state some of the molecular order characteristics of the solid phase are retained in the liquid state because of the molecular association structure and long range intermolecular interaction. The ability of some compounds to form a mesophase, typically referred to as liquid crystals, was observed nearly a century ago.

Thermotropic liquid crystals are obtained by heating solid crystals at a temperature above which they are no longer stable. Such thermotropic liquid crystals are well known in our day-to-day life, and have multiple applications as they exhibit variations in color with temperature and/or a magnetic field and/or an electric field. They are formed by elongated molecules and are used in some cosmetics for their visible impact (visualization of actives). Lyotropic liquid crystals result from the interaction with a solvent over a particular range of concentration and temperature. Low molecular weight lyotropic liquid crystals, i.e. liquid crystals formed from a low molecular weight emulsifier or organic amphiphile (a compound having both a polar and a nonpolar group, as a soap, lecithins or long chain fatty acid monoglyceride), are known to encapsulate and act as a delivery vehicle for drugs, flavors, nutrients and other compounds.

The association structures of the present invention are:
a) Reverse Micelles:
  (1) Reverse micelles also known in the art as spherical reverse micelles, elongated reverse micelles, bicontinuous phase or L2 phase; and
  (2) Cylindrical reverse micelles or reverse connected rod-shaped liquid crystals also known in the art as networking reverse cylinders, connected cylindrical reverse micelle structures, or connected cylinders; and
b) Lyotropic Liquid Crystals:
  (1) Reverse hexagonal liquid crystals also known in the art as Hexognal II or F phase;
  (2) Cubic liquid crystals also known in the art as viscous isotropic and $I_2$ phase; and
  (3) Lamellar liquid crystals also known in the art as the La neat phase and D phase.

The association structure of the present invention is selected from the group consisting of reverse micelles, lyotropic liquid crystals and mixtures thereof.

Preferred association structures are the cylindrical reverse micelle, reverse hexagonal liquid crystals, cubic liquid crystals, lamellar liquid crystals and mixtures thereof. The most preferred association structures are lamellar liquid crystals, reverse hexagonal liquid crystals and mixtures thereof. The association structures can be in the following phases: two phase liquid crystals, one phase liquid crystals, reverse micelles/liquid crystalline phase or liquid crystalline/solvent phase. Preferably the liquid crystals are substantially one phase or two liquid crystalline phases, i.e., at least about 90%, more preferably about 98% and most preferably at least about 99%, of the association structure is in the form of the liquid crystal.

The association structures comprise from about 0.1% to about 80% of the lipstick composition. Preferably the association structures comprise from about 3% to about 75%, more preferably from about 10% to about 65%, and most preferably form about 30% to about 60% of the lipstick composition comprises the association structures, preferably lamellar liquid crystals.

Polar Solvents

The solvents useful for making the association structures of the present invention include any polar solvent acceptable for human ingestion. Suitable polar solvents include: water; alcohols, such as ethanol, propyl alcohol, isopropyl alcohol, hexanol, and benzyl alcohol; polyols, such as propylene glycol, polypropylene glycol, butylene glycol, maltitol, sorbitol, and glycerine; panthenol dissolved in glycerine; flavor oils, and mixtures thereof. Mixtures of these solvents can also be used. Preferred polar solvents are glycerine, panthenol in glycerine, propylene glycol, butylene glycol, water and mixtures thereof. Most preferably, water added by itself, i.e. other than the water present in commercially supplied solvents, is not utilized. Thus, the most preferred lipstick compositions of the present invention are essentially free of water, i.e., less than about 3% and preferably less than about 1%. The most preferred polar solvents for use are glycerine, panthenol, propylene glycol, butylene glycol and mixtures thereof.

The solvents are used at levels of from about 3% to about 96%, preferably from about 5% to about 95%, more preferably from about 10% to about 80% and most preferably from about 30% to about 70% of the association structure. Typically, the lipstick compositions will comprise from about 0.1% to about 60%, preferably from about 1% to about 30% and most preferably from about 8% to about 18% polar solvent.

Surfactants

Surfactants suitable for use are those which can form association structures, preferably lamellar liquid crystals or reverse hexagonal, at ambient temperature when mixed with a polar solvent. Ambient temperature/room temperature as used herein typically means about 20° C. Generally ambient temperature can range from about 18° C. to about 27° C., preferably from about 20° C. to about 25° C., depending on such variables as geographical location, i.e. sub-tropical vs. temperate regions. One of ordinary skill in the art is able to determine if association structures form at ambient temperatures. The surfactants suitable for use generally have a Krafft point at or below about ambient temperature about 20° C. or generally at or below about 18° C. to about 27° C., preferably at or below from about 20° C. to about 25° C.

The definition of Krafft point is well known in the art and one of ordinary skill in the art can determine a surfactant's Krafft point. In general terms, Krafft point is the melting point of the hydrocarbon chains of the surfactants. It can also be expressed as the temperature at which the solubility of an association colloid in water suddenly increases because critical micelle concentration is exceeded and micelles form. See Ekwall., P., "Composition, Properties and Structure of Liquid Crystalline 1Phases in Systems of Amphiphilic Compounds" Advances in Liquid Crystals Vol. I, Chapter I, p.81.

In preparing a sample combination of surfactant and polar solvent to demonstrate the ability to form association structures, the surfactant needs to be sufficiently soluble in the polar solvent such that an association structure can form at ambient temperature. One of ordinary skill in the art is capable of determining compatible interactions.

Any surfactant which forms association structures at ambient temperature and is suitable for use in cosmetics is suitable for use herein. Surfactants suitable for use in cosmetics do not present dermatological or toxicological problems. Anionic surfactants, nonionic surfactants, cationic surfactants, amphoteric surfactants and mixtures thereof are suitable for use. Preferably anionic surfactants, nonionic surfactants, cationic surfactants, amphoteric surfactants and mixtures thereof having a Krafft point at or below about ambient temperature are used. More preferably, nonionic surfactants, cationic surfactants, amphoteric surfactants and mixtures thereof having a Krafft point at or below about ambient temperature are used.

Types of anionic surfactants suitable for use are soaps; sulfonates such as alkane sulfonates (e.g., branched sodium x-alkane sulfonate where x≠1) paraffin sulfonates, alkylbenzene sulfonates, a-olefin sulfonates, sulfosuccinates and sulfosuccinate esters (e.g., dioctylsodium and disodium laureth sulfosuccinate), oisethionates, acylisethionates (e.g., sodium 2-lauroyloxyethane sulfonate), and sulfalkylamides of fatty acids, particularly N-acylmethyltaurides; sulfates such as alkyl sulfates, ethoxylated alkyl sulfates, sulfated monoglycerides, sulfated monoglycerides, sulfated alkanolamides, and sulfated oils and fats; carboxylates such as alkyl caboxylate having a carbon chain length above $C_{12}$, acylsarcosinates, sarcosinates (e.g., sodium lauryl sarcosinate), ethoxylated carboxylic acid sodium salts, carboxylic acids and salts (e.g., potassium oleate and potassium laurate), ether carboxylic acids; ethoxylated carboxylic acids and salts (e.g., sodium carboxymethyl alkyl ethoxylate; phosphoric acid esters and salts (e.g., lecithin); acylglutamates (e.g., disodium n-lauroyl glutamate) and mixtures thereof. It should be noted that the safest alkyl sulfates for use generally have a hydrocarbon chain lengths above $C_{12}$.

Types of nonionic surfactants suitable for use are polyoxyethylenes such as ethoxylated fatty alcohols, ethoxylated alcohols (e.g., octaoxyethelene glycol mono hexadecyl ether, $C_{16}E_8$ and $C_{12}E_8$), ethoxylated fatty acids, ethoxylated fatty amines, ethoxylated fatty amides, ethoxylated alkanolamides, and ethoxylated alkyl phenols; triesters of phosphoric acid (e.g., sodium dioleylphosphate); alkyl amido diethylamines; alkylamido propylbetaines (e.g., cocoamido propylbetaine); amine oxide derivatives such alkyl dimethylamine oxides, alkyl dihydroxyethylamine oxides, alkyl amidodimethylamine oxides and alkyl amidodihydroxyethylamine oxides; polyhydroxy derivatives such as polyhydric alcohol esters and ethers (e.g., sucrose monooleate, cetostearyl glucoside, β octyl glucofuranoside, esters, alkyl glucosides having a carbon chain length of from $C_{10}$ to $C_{16}$), mono, di- and polyglycerol ethers and polyglycerol esters (e.g., tetraglycerol monolaurate and monoglycerides, triglycerol monooleate (such as TS-T122 supplied by Grinsted), diglycerol monooleate (such as TST-T122 supplied by Grinsted), ethoxylated glycerides; monoglycerides such as monoolein anld monlinolein; diglyceride fatty acids such as diglycerol monoisostearate (e.g., Cosmol 41 fractionated supplied by Nisshin oil Mills, Ltd.) and mixtures thereof.

Types of cationic surfactants suitable for use are aliphatic-aromatic quaternary ammonium halides; quaternary ammonium alkyl amido derivatives; alkyl amidopropyldimethylammonium lactate; alkylamidopropyldihydroxyethylammo-nium lactate; alkyl amidopropyl morpholinium lactate; quaternary ammonium lanolin salts; alkyl pyridinium halides; alkyl isoquinolinium halides; alkyl isoquinolinium halides; quaternary ammonium imidazolinium halides; bisquaternary ammonium derivatives; alkylbenzyl dimethylammonium salts such as stearalkylammonium chloride; alkylbetaines such as dodecyldimethylammonium acetate and oleylbetaine; alkylethylmorpholinium ethosulfaates; tetra alkyl ammonium salts such as dimethyl distearyl quaternary ammonium chloride and bis isostearamideopropyl hydroxypropyl diammonium chloride (Schercoquat 2IAP from Scher Chemicals); heterocyclic ammonium salts; bis(triacetylammoniumacetyl) diamines and mixtures thereof.

Types of amphoteric surfactants suitable for use are alkyl betaines; alkanolamides such as monoalkanolamides and dialkanolamides; alkyl amido propylbetaines; alkyl amidopropylhydroxysultaines; acylmonocarboxy hydroxyethyl glycinates; acyldicarboxy hydroxyethyl glycinates; alkyl aminopropionates such as sodium laurimino dipropionate; alkyl iminodipropionates; amine oxides; acyl ethylenediamine betaines; N-alkylamino acids such as sodium N-alkylamino acetate; N-lauroylglutamic acid cholesterol esters; alkyl imidazolines and mixtures thereof.

Preferred anionic surfactants for use are sulfosuccinate esters, isethionates, sarcosinates, sodium lauryl sulfoacetate, phosphate esters, alkyl carboxylates having a hydrocarbon chain length above $C_{12}$, acylglutamates and mixtures thereof.

Most preferred for use are nonionic surfactants. Examples of preferred nonionic surfactants are carbohydrate surfactants such as sucrose monoester and alkyl glucosides; polyglycerol esters such as tetraglycerol monolaurate PG-3 diisostearate, triglycerol monooleate, and diglycerol monooleate; monoglycerides; diglycerol esters such as PG-2 monoisostearate, PG-2 monooleate, PG-2 monostearate, PG2 diisostearate, and PG-2 dioleate; sorbitan esters and mixtures thereof.

Preferred surfactants for use are polyhydricalcohol esters and ethers such as sucrose monooleate, cetoarylglucoside, cetostearylglucoside, alkylglucosides having a carbon chain length of from $C_{10}$ to $C_{16}$, β octyl glucofuranosides; polyglycerol esters such as tetraglycerol monooleate or laurate; monoglycerides such as monoolein; phosphatides such as lecithin; bis isostearamidopropyl hydroxypropyl diammonium chloride; sorbitan oleate; dipentaerythritol fatty acid ester; n-lauroyl glutamic acid ester; tetra glycerol monolaurate; and mixtures thereof.

A variety of lecithins can be used. American Lecithin Company (Danbury, Conn.) supplies a Nattermann Phospholipid, Phospholipon 80 and Phosal 75. All of these function well in this system. Other lecithins which can be used alone or in combination with these are: hydrogenated lecithin supplied by Nisshin Oil Mills, Ltd; Actiflo Series, Centrocap series, Central Ca, Control series, Centrolene, Centrolex, Centromix, Centrophase and Centrolphil Series from Central Soya (Ft. Wayne, Ind.); Alcolec and Alcolec 439-C from American Lecithin; Canasperse form Canada Packers, Lexin K and Natipide from American Lecithin; and L-Clearate, Clearate LV and Clearate WD from the W. A. Cleary Co. Lecithins are supplied dissolved in ethanol, fatty acids, triglycerides and other solvents. They are usually mixtures of lecithins and range from 15% to 75% of the solution as supplied. The lecithins are also supplied as powders. The purity of the powder varies, but the lecithin can be from 60% to 90% of the powder on a weight basis. The weight of phosphatide as used herein is the weight of the lecithin and not of the carriers or impurities.

In order to form the appropriate type of association structure, the lecithin must be sufficiently soluble in the polar solvent such that a liquid crystalline state can be formed at the temperature conditions of product preparation. Additionally, the lecithin association structures should be of a type which has the capability to flow under application of shear, preferably lamellar, hexagonal II (reverse hexagonal) or mixtures thereof.

Both natural and synthetic lecithins can be used. Natural lecithins are derived from oilseeds such as sunflower seeds, soybeans, safflower seeds and cottonseed. The lecithins are separated from the oil during the refining process. Eggs are also a natural source of lecithin.

The phosphatide can be used at a level of from about 25% to about 95%, preferably from about 30% to about 85% and most preferably from about 40% to about 70% of the association structure. Preferably a mixture of a phosphatide with other surfactants capable of forming associations structures is used. When such a mixture is used the phosphatide is preferably used at levels of from about 0.1% to about 30%, preferably from about 0.1% to about 5% and more preferably from about 0.1% to about 1% of the lipstick composition. Most preferably lecithin is not utilized as an association structure forming surfactant, i.e., essentially free of lecithin (>0.01%).

Typically when utilizing a phosphatide as the surfactant for forming an association structure at levels of less than about 30% of the association structure, reverse micelles, cylindrical reverse micelles, reverse connected rod-shaped liquid crystals, and mixtures of these association structures will be formed. Typically when utilizing a phosphatide at greater than about 30% of the association structure, the preferred lamellar (L2) phase association structures will be formed.

Typical Formulations Can Utilize the Following
Amphoteric
N-alkyl amino acids (e.g., sodium N-alkylaminoacetate)
N-lauroylglutamic acid cholesterol ester (e.g., Eldew CL-301 Ajinomoto)
Anionic
Acylglutamates (e.g., disodium N-lauroylglutamate)
Sarcosinates (e.g., sodium lauryl sarcosinate) (Grace, Seppic)
Tauratas (e.g., sodium lauyl taurate, sodium methyl cocoyl taurate)
Carboxylic acids and salts (e.g., potassium oleate, potassium laurate, potassium-10-undecenoate; potassium, 11-p-Styryl)-undecanoate
Ethoxylated carboxylic salts (e.g., sodium carboxy methy-alkyl ethoxylate)
Ether carboxylic acids
Phosphoric acid esters and salts (e.g., lecithin) DEA-oleth-10 phosphate
Acyl isethionates such as sodium 2-lauroyloxyethane sulfonate
Alkane sulfonates (e.g., branched sodium x-alkane sulfonate (x/1)
Sulfosuccinates e.g. dioctyl sodium sulfosuccinate; disodium laureth sulfosuccinate (MacKanate El, McIntyre Group Ltd.)
Sulfosuccinates (aerosols)
  Sodium dibutyl sulfosuccinate
  Sodium Di-2-pentyl sulfosuccinate
  Sodium Di-2-ethylbutyl sulfosuccinate
  Sodium Di hexyl sulfoscuccinate
  Sodium Di-2-ethylhexyl sulfosuccinate (AOT)
  Sodium Di-2-ethyldodecyl sulfosuccinate
  Sodium Di-2-ethyloctadecyl sulfoscuccinate
Sulfuric acid esters, e.g., sodium 2-ethylhept-6-ENYL sulfate; sodium 11-Heneicosyl sulfate; sodium 9-Heptadecyl sulfate
Alkyl sulfates e.g., MEA alkyl sulfate such as MEA-lauryl sulfate
Cationic
Alkyl Imidazolines such as alkyl hydroxyethyl imidazoline, stearyl hydroxyethyl imidazoline (supplier Akzo, Finetex and Hoechst)
Ethoxylated Amines such as PEG-n alkylamine, PEG-n alkylamino propylamine, Poloxamine e.g, PEG-cocopolyamine, PEG-15 tallow amine
Quaternaries: Alkylbenzyl dimethyl ammonium salts, betaines, heterocyclic ammonium salts and tetra alkylammonium salts.
Alkylamines, dimethyl alkylamine, dihydroxyethyl alkylamine dioleate
Alkylbenzyl dimethylammonium salts (e.g., stearalkyl ammonium chloride)
Alkyl betaines (e.g., dodecyl dimethyl ammonio acetate, oleyl betaine)
Alkyl ethyl morpholinium Ethosulfate
Tetra alkyl ammonium salts (e.g., dimethyl distearyl quaternary ammonium chloride (Witco))
Bis isostearamidopropyl hydroxy propyl diammonium chloride (Schercoquat 2IAP from Scher Chemicals)
1,8-Bis(decyldimethylammonio)-3,6 dioxaoctane ditosylate
Nonionic Surfactants
Ethoxylated glycerides
monoglycerides such monoolein, monolinolein, monolaurin
diglyceride fatty acid (e.g., diglycerol monoisostearate Cosmol 41, fractionated, Nisshin Oil Mills Ltd.)
Polyglyceryl esters (e.g., triglycerol monooleate (Grindsteal TS-T122), diglycerol monooleate (Grindsted TST-T101)
Polyhydric alcohol esters and ethers (e.g., sucrose monooleate (Ryoto, Mitsubishi-Kasei Food Corp.) ceto-stearyl glucoside (Montanol, Seppic), β octyl glucofuranoside esters, alkyl glucoside such $C_{10}$–$C_{16}$ (Henkel)
Diesters of phosphoric acid (e.g., sodium dioleyl phosphate)
Ethoxylated alcohols (e.g., $C_{16}E_8$ (octaoxyethylene, glycol mono hexadecyl ether) and $C_{12}E_8$)
Alkylamido propyl betaine (e.g., cocoamide propyl betaine)
Amide: (e.g., N-(doderanoylaminoethyl)-2-pyrrolidone)
Amide oxide: e.g., 1,1 Dihydroperfluorooctyldimethylamine oxide
  Doderyldimethylamine oxide
  2-Hydroxydodecyldimethylamine oxide
  2-Hydroxydodecyl-bis(2-hydroxyethyl)amide oxide
  2-Hydroxy-4-oxahexadecyldimethylamine oxide
Ethoxylated amides (e.g., PEG-n acylamide)
Nonionic
Amnonio phosphates (e.g., didecanoyl lecithin)
Amine (e.g., octylamine)
Ammonio amides e.g.,
  N-trimethylammoniodecanamidate
  N-trimethylammoniododecanamidate
Ammonio carboxylates e.g.,
  dodecyldimethylammonioacetate
  6-didodecymethylammoniohexanoate
Monoglycerides e.g.,
  1 dodecanoyl-glycerol monolaurin
  1-13-docosenoyl-glycerol monoerucin
Phosphonic and phosphoric esters and amides e.g.,
  methyl-N-methyl-dodecylphosphonamidate
  dimethyl dodecylphosphonate
  dodecyl methyl methylphosphonate
  N,N-dimethyl dodecylphosphonic diamide
Polyoxyethylene (C8) e.g.,
  pentaoxyethylene Glycol p-n-octylphenyl ether
  hexaoxyethylene Glycol p-n-octylphenyl ether
  nonaoxyethylene Glycol p-n-octylphenyl ether
Polyoxyethylene (C10) e.g.,
  pentaoxyethylene Glycol p-n-decylphenyl ether
  decyl Glyceryl ether, 4-oxatetradecan-1,2-diol
  nonaoxyethylene glycol p-n-decylphenyl ether
Polyoxyethylene (C11) e.g.,
  Tetraoxyethylene glycol undecyl ether
Polyoxyethylene (C12) e.g.,
  3,6,9,13-tetraoxapentacosan 1,11-diol
  3,6,10-trioradocosan-1,8,diol
  3,6,9,12,16-pentaoxaoctacosan 1,14-diol
  3,6,9,12,15-pentaoxanonacosan-1,17-diol
  3,7-dioxanonadecan-1,5-diol
  3,6,9,12,15,19-hexaoxahentriacontan-1,16-diol pentaoxyethylene glycol dodecyl ether
monaoxyethylene glycol p-n-dodecylphenyl ether
Polyoxyethylene (C14) e.g.,
   3,6,9,12,16-pentaoxaoctacosan-1,14-diol
   3,6,9,12,115,1 9-heraoxatriacontan-1,17-diol
Sulfone diimines e.g.,
   decyl methyl sulfone diimine
Sulfoxides e.g.,
   3-decyloxy-2-hydroxypropyl methyl sulfoxide
   4-decyloxy-3-hydroxybutyl methyl sulfoxide
Sulfoximines e.g.,
   N-methyl dodecyl methyl sulfoximine
More Preferred for Use Commercially available cationic surfactants suitable for use are: Abil B9950, Polysiloxane Betaine supplied by Goldschmidt; Arquat 2H-75 supplied by Akzo; Schercoquat 21AP supplied by Scher. Chem.; and Schercoquat DAS supplied by Scher Chem. Commercially available anionic surfactants suitable for use are: Crodafos N10 supplied by Croda and Dioctyl Sodium Sulfosuccinate supplied by American Cyanimid. Commercially available nonionic surfactants suitable for use are: Crodesta F-50, Sucrose Distearate supplied by Croda; Diglycerol monoisostearate, Cosmol 41, Fractionated supplied by Nisshin; Dimodan DGMO and Triodan 20 supplied by Grindsted; Generol 122 E-10 Ethoxylated Soya Sterol, Generol E-16 and Generol E-5 supplied by Henkel; Mirasoft MSP-011 supplied by Rhone-Poulenc; Montanol 68 Ecailles (cetearyl glucoside) supplied by Seppic; Sucrose Monooleate supplied by Mitsubishi; and Tetraglycerol Laurate supplied by Lonza. A commercially available amphoteric surfactant suitable for use is Eldew CL-301 supplied by Ajinomoto.

The surfactants can be used at levels from about 4% to about 97%, preferably from about 5% to about 95%, more preferably from about 20% to about 90% and most preferably from about 30% to about 70% of the association structure.

Preparation of the Association Structure

Formation of the association structure, i.e., reverse micelles and/or liquid crystals and the concentration at which such association structures occur is dependent upon a variety of factors, including the specific types of surfactant, solvent, temperature, solubility of the surfactant in the solvent, and concentration of the surfactant in the carrier. The purity of the surfactant affects the concentration level at which the association structures and particularly the preferred form of lamellar liquid crystals form.

The polar solvent and surfactant are mixed together. Formation of the association structure, particularly the preferred lamellar or hexagonal liquid crystalline state is accelerated by mechanical agitation. Mixing, can be performed either by hand (i.e., using hand utensils) or with mechanical equipment useful for home, institutional, or industrial lipstick preparation. Extruders which provide a shearing operation with mixing can be used.

Generally the association structures are formed at ambient temperature/room temperature. The processing temperature will depend somewhat on the properties of the polar solvent. However, during processing the association structures will be exposed to temperatures in the range of from about 10° C. to about 100° C., preferably from about 70° C. to about 90° C. If the temperatures affect the association structures, the association structures will reform once cooled to ambient temperature.

The one-phase liquid crystal is most preferred. It is preferred that a substantially two phase liquid crystal, one-phase liquid crystal or single phase liquid crystal component of (preferably at least 90%) be utilized.

Separation and thus detection of the association structure from excess liquid (solvent or solution) or solid may be achieved by ultracentrifugation. Ultracentrifugation should be conducted using sufficiently high centrifugal forces (preferably within the range of from about 20,000 rpm to about 60,000 rpm for from about one hour to about sixteen hours utilizing a Beckman L8-80 centrifuge equipped with a SW60Ti Rotor or by applying about 300,000*g for about one hour) to induce the formation of observable phase boundaries over a period of time. Under these conditions a good separation of the individual phases is obtained. The volume of each phase is determined by calibration of the centrifuge tube and the volume fraction of the individual phase thus calculated.

Wax

The wax acts as a solidifying agent in the lipstick. It assists in the formation of the solid structure of the lipstick. The wax is comprised of organic compounds or mixtures of high molecular weight substances, and is solid at ambient temperature/room temperature. The wax can be hydrocarbons or esters of fatty acids and fatty alcohols. Waxes are thermoplastic. Natural, mineral and synthetic waxes can be used herein. As used herein "wax" refers to mixtures as well as a single type of wax.

Natural waxes can be of animal origin, e.g. beeswax, spermaceti, lanolin, shellac wax, or of vegetable origin, e.g. carnauba, cadelilla, bay berry, sugarcane wax, and of mineral origin, e.g. ozokerite, ceresin, montan, paraffin, microcrystalline wax, petroleum and petrolatum wax. Synthetic waxes include polyol ether-esters such as carbowax and hydrocarbon-type waxes, silicone waxes and polyethylene wax. Generally, the waxes useful herein have melting points from about 55° C. to about 110° C. and are selected from the $C_8$ to $C_{50}$ hydrocarbon waxes.

The preferred waxes of the present invention are selected from the group consisting of candelilla, beeswax, carnauba, spermaceti, montan, ozokerite, ceresin, paraffin, modified beeswax, bayberry, castor waxes, synthetic waxes, microcrystalline waxes and mixtures thereof. More preferably the waxes are selected from the group consisting of microcrystalline, spermaceti, candelilla, modified beeswax, carnauba, ozokerite, paraffin, ceresin, and mixtures thereof. Most preferably, the waxes are selected from the group consisting of microcrystalline, candelilla, modified beeswax, ozokerite, paraffin, and mixtures thereof. A particularly preferred mixture of waxes used in the present invention is as follows:
   a. from about 3% to about 6% candelilla wax;
   b. from about 2% to about 5% ozokerite wax;
   c. from about 2% to about 5% paraffin wax; and
   d. from about 1% to about 4% microcrystalline wax.

The amount of wax used is from about 5% to about 90%, preferably from about 10% to about 30% and most preferably from about 10% to about 20% of the lipstick composition.

Emollient Component

The emollient component can comprise fats, oils, fatty alcohols, fatty acids and esters which aid application and adhesion, yield gloss and most importantly provide occlusive moisturization. The removal of castor oil from the preferred lipstick compositions of the present invention allows the utilization of more emollients.

Suitable emollients for use are isostearic acid derivatives, isopropyl palmitate, surfactants, lanolin oil, diisopropyl dimerate, maleated soybean oil, octyl palmitate, isopropyl isostearate, octyl hydroxystearate, cetyl lactate, cetyl ricinoleate, tocopheryl acetate, acetylated lanolin alcohol, cetyl acetate, lecithin, phenyl trimethicone, glyceryl oleate, tocopheryl linoleate, wheat germ glycerides, arachidyl propionate, isopropyl palmitate, myristyl lactate, decyl oleate, propylene glycol ricinoleate, isopropyl lanolate, pentaerythrityl tetrastearate, neopentylglycol dicaprylate/ dicaprate, hydrogenated cocoglycerides, isotridecyl isononanoate, myristal myristate, triisocetyl citrate, cetyl alcohol, octyl dodecanol, oleyl alcohol, panthenol, lanolin alcohol, linoleic acid, linolenic acid and mixtures thereof.

Polar solvent/moisturizing agents in excess of the polar solvents forming association structures can be used in the emollient component. When these excess polar solvents are utilized in the emollient component, it is preferred that a coupling agent also be used. Glycerine is a preferred moisturizer and preferably forms a part of the association structure system. Other preferred moisturizers include pyrrolidone carboxylic acid, sodium lactate or lactic acid, urea collagen, α-hydroxy propylglyceryl ether α-hydroxy acids (e.g., ethylglycolic acid, leucic acid, mandelic acid, glycollic acid), glucosamines, and elastin fibers, D-panthenol, aklantoin and hyaluronic acid and chondroitin sulfate. Please note that some of these can be delivered with the association structures by dissolving into the polar liquid.

Oils are those materials which are organic substances that are liquid at ambient temperature. They are esters, triglycerides, hydrocarbons and silicones. These can be a single material or a mixture of one or more materials. They will normally comprise from 0% to about 100%, preferably from about 5% to about 90%, and most preferably from about 70% to about 90% of the emollient component.

Preferably, the oils are minimized in the present invention due to their tendency to sweat. A preferred embodiment of the present invention utilizes a coupling agent when the compositions comprise greater than about 40% oil. The oils act as emollients and also impart viscosity, tackiness, and drag properties to the lipstick. Suitable oils include caprylic triglycerides; capric triglyceride; isostearic triglyceride; adipic triglyceride; propylene glycol myristyl acetate; lanolin; lanolin oil; polybutene; isopropyl palmitate; isopropyl myristate; isopropyl isostearate; diethyl sebacate; diisopropyl adipate; tocopheryl acetate; tocopheryl linoleate; hexadecyl stearate; ethyl lactate; cetyl oleate; cetyl ricinoleate; oleyl alcohol; hexadecyl alcohol; octyl hydroxystearate; octyl dodecanol; wheat germ oil; hydrogenated vegetable oils; petrolatum; modified lanolins; branched-chain hydrocarbons; alcohols and esters; corn oil; cottonseed oil; olive oil; palm kernel oil; rapeseed oil; safflower oil; jojoba oil; evening primrose oil; avocado oil mineral oil, sheabutter, octylpalmitate, maleated soybean oil, glycerol trioctanoate, diisopropyl dimerate, and volatile and non-volatile silicone oils including phenyl trimethicone. Castor oil is not preferred for use herein. Preferred lipstick composition of the present invention are substantially free of castor oil such that the lipstick comprises less than about 0.1%, preferably less than about 0.01% and most preferably less than about 0.001% of castor oil.

The preferred oils for use herein are caprylic triglycerides, capric triglycerides, isostearic triglyceride, adipic triglyceride, phenyl trimethicone, lanolin oil, polybutene, isopropyl palmitate, isopropyl isostearate, cetyl ricinoleate, octyl dodecanol, oleyl alcohol, hydrogenated vegetable oils, modified lanolins octyl palmitate, lanolin oil, maleated sooybean oil, cetylricinoleate, glyceryltrioctanoate diisopropyl dimerate, synthetic anolin derrivatives and branched chain alcohols and mixtures thereof.

Preferably, the oils used are selected such that the majority (at least about 75%, preferably at least about 80% and most preferably at least about 99%) of the types of oils used have solubility parameters which do not differ by more than from about 1 to about 0.3, preferably from about 0.8 to about 0.5. For example, the more preferred oils for use are lanolin oil, octyl palmitate and isopropylpalmitate. Their respective solubility parameters are 7.3, 7.4 and 7.8. Thus, the solubility parameters do not differ by more than about 0.5. (Solubility parameters as reported in "Cosmetics & Toletries", Vol 103, October 1988, p64.) It is also preferred that the oils and waxes utilized have compatible solubilities.

The more preferred oils for use herein have a solubility parameter of from about 7.3 to abut 7.8. Examples of more preferred oils for use herein are lanolin oil, octyl palmitate, isopropylpalmitate and mixtures thereof.

The emollient component comprises from about 1% to about 90%, preferably from about 10% to about 80%, more preferably from about 20% to about 70%, and most preferably from about 40% to about 60%, of the lipstick composition.

Color

The lipsticks can contain from 0% to about 35% preferably from about 1% to about 20% and most preferably from about 5% to about 15%, of color, on an anhydrous pigment weight basis. These are usually aluminum, barium or calcium salts or lakes. Preferably, dyes are present at from about 0.1% to about 4% and pearls from 0% to about 20%. Colors which are dispersed in castor oil are not preferred for use.

Preferably, the lipstick compositions of the present invention are substantially free of castor oil such that the lipstick comprises less than about 0.1%, preferably less than about 0.01% and most preferably less than about 0.001% castor oil.

Pigments are typically dispersed in castor oil for the good dispersion of the pigments when incorporated into the lipstick, thus providing an even distribution of color. It has been discovered that excellent dispersion of the pigment can be achieved by utilizing the association structures, preferably lamellar liquid crystals, as a means of incorporating the color/pigments into the lipstick. A preferred method of incorporating dry pigments comprises the steps of:

(a) preparing a mixture consisting essentially of:
 (1) a polar solvent; and
 (2) a surfactant selected from the group consisting of amphoteric, cationic, anionic and nonionic surfactants having a Krafft point at or below about ambient temperature and mixtures therof; and (b) stirring said mixture until association structures form;

(c) adding and mixing dry pigments until achieving a homogenous mixture;

(d) milling said mixture until uniform particle size is acheived; and (e) adding and mixing the mixture of (c) to the remaining lipstick ingredients until a homogenous mixture is obtained.

If the ingredients of the lipstick composition are being processed such that the association structures are being formed in situ, the preferred method of incorporating the dry pigments is to slurry them in one or more of the liquid emollient ingredients.

It should be noted that during processing of the association structure lipstick compositions, there is an improvement in the form of a noted decrease in the amount of separation of pigment particles during processing and molding.

Colors/pigments suitable for use herein are all inorganic and organic colors/pigments suitable for use in lipstick compositions.

Lakes are either a pigment that is extended or reduced with a solid diluent or an organic pigment that is prepared by the precipitation of a water-soluble dye on an adsorptive surface, which usually is aluminum hydrate. There is uncertainty in some instances as to whether the soluble dye precipitates on the surface of the aluminum hydrate to yield a dyed inorganic pigment or whether it merely precipitates in the presence of the substrate. A lake also forms from precipitation of an insoluble salt from an acid or basic dye. Calcium and barium lakes are also used herein.

Preferred lakes of the present invention are Red 3 Aluminum Lake, Red 21 Aluminum Lake, Red 27 Aluminum Lake, Red 28 Aluminum Lake, Red 33 Aluminum Lake, Yellow 5 Aluminum Lake, Yellow 6 Aluminum Lake, Yellow 10 Aluminum Lake, Orange 5 Aluminum Lake and Blue 1 Aluminum Lake, Red 6 Barium Lake, Red 7 Calcium Lake.

Other colors and pigments can also be included in the lipsticks, such as dyes and pearls, titanium oxides, Red 6, Red 21, Brown, Russet and Sienna dyes, chalk, talc, iron oxides and titanated micas.

Other Additives

Optional ingredients which can be present in the lipstick include the flavor oils which were described above, fat soluble vitamins such as vitamin A and E, sunscreens and skin care actives. The lipstick can comprise ingredients conventionally employed in lipsticks or other lipcare products. This includes skin care active ingredients such as pharmaceutically active ingredients.

Flavor oils such as peppermint oil, orange oil, citrus oil, wintergreen oil can be used along with an alcohol or glycerine. Flavor oils are usually mixed in a solvent such as ethanol to dilute the flavor. The flavor oils useful herein can be derived from natural sources or be synthetically prepared. Generally flavor oils are mixtures of ketones, alcohols, fatty acids, esters and terpenes. The term "flavor oil" is generally recognized in the art to be a liquid which is derived from botanical sources, i.e. leaves, bark, or skin of fruits or vegetables, and which are usually insoluble in water. The level of flavor oil used can range from 0% to about 5%, preferable from 0% to about 1%.

Emulsifiers do not form association structures at ambient temperature with the polar solvent utilized therein can also be used. The overall concentration of the emulsifier can be from 0% to about 20% of the formulation, preferably from 0% to about 15% and most preferably from about 1% to about 10%.

These emulsifiers are used as a coupling agents which have an affinity for the hydrophilic (not the polar solvent) and hydrophopic phases of the lipsticks, yet do not form association structures at ambient temperature. Examples of suitable coupling agents are sorbitan oleate, sorbitan sesquioleate, PG-3 diisostearate, dipentaerythritol fatty acid ester, cholesteral 12 hydroxystearate, and mixtures thereof.

A preferred embodiment of the present invention comprises from about 0.1% to about 30%, preferably from about 8% to about 15%, polar solvent and from about 5% to about 20%, surfactants of the lipstick composition. The surfactants are preferably a mixture wherein from about 50% to about 75% of the mixture is made up of surfactants which have a Krafft point of at or below about ambient temperature and form association structures at ambient temperature and from about 25% to about 50% of the mixture is made up of surfactants which are coupling agents. Another preferred mixture of surfactants which can form association structures and surfactants which act as coupling agent is lecithin, PG-3 diisosterate, sorbitgonleate, cholesterol 12 hydroxystearate and dipentaerythritol fatty acid ester. Another preferred mixture is dipentaerythritol fatty acid ester, lecithin, and PG-3 diisosterate.

Skin care actives ingredients in both water soluble and water insoluble forms can be added to the lipstick. These include zinc oxide, beta-glycyerhetic acid; chamomile oil; ginko biloba extract; pyroglutamic acid, salts or esters; sodium hyaluronate; 2-hydroxyoctanoic acid; sulfur; salicylic acid; carboxymethyl cysteine, and mixtures thereof. These will normally be present in amounts of less than about 2% by weight, and generally in the range of about 0.01% to about 1% by weight.

A preferred optional component is ethyl cellulose (Ethocel). Ethyl cellulose generally is preferred for use at levels of about 5% and more preferably 1%. Another preferred optional component is silica. Silica is generally preferred for use at levels of from about 1% and about 5%.

Hypoallergenic Lipsticks

Hypoallergenic lipsticks can be made from the liquid crystal, wax, oil and colors herein. These lipsticks should not contain fragrances, flavor oils, lanolin, sunscreens, particularly PABA, or other sensitizers and irritants.

Addition of the association structure to lipsticks

The association structure can be used in conventional lipstick formulating as a substitute for castor oil, other oils, and other lipstick ingredients. The association structures can be formed before addition or the polar solvent component and surfactant component of the association structure can be added independently and the association structures will form in situ. Preferably from 10% to 60%, preferably from about 20% to about 50%, of the oil or wax component is replaced with the stable liquid crystal. Generally lipstick formulations can be adjusted without undue experimentation.

The association structure should be well mixed with the solid component of the composition. It is preferable to prepare the association structures first, preferably liquid crystals or reverse hexagonal liquid crystals and more preferably lamallar liquid crystals, and then mix the association structures with the waxes and oils in order to most effectively achieve a microscopic distribution of the association structure in the solid.

The association structures, preferably lamellar liquid crystals and/or reverse hexagonal liquid crystals, can be mixed with the waxes while they are molten and the mixture molded by conventional means. Preferably, the waxes and emollient component are melted at a temperature of from about 70° C. to about 95° C., preferably from about 83° C. to 90° C. and the association structure is added with stirring. The mixture is then poured into a mold at room temperature. The molding temperature can be varied to give a more uniform stick. Other conventional lipstick making processes can be used.

The following examples illustrate the invention but are not intended to be limiting thereof.

EXAMPLE I

A lipstick composition of the present invention which is substantially free of castor oil, is prepared as follows:

| Ingredient | Amount (weight percent) |
| --- | --- |
| Carnauba | 1.50 |
| Ozokerite | 6.00 |
| Candelillia | 4.00 |
| Hydrogenated Vegetable Oil | 5.00 |
| Acetylated Lanolin | 4.00 |

-continued

| Ingredient | Amount (weight percent) |
|---|---|
| Isopropyl Isostearate | 11.90 |
| Isostearic Acid | 10.00 |
| Propylparaben | 0.10 |
| Cetyl Ricinoleate | 10.00 |
| Ascorbyl Palmitate | 1.00 |
| Silica L-700 | 1.00 |
| Polybutene | 2.00 |
| Petrolatum | 5.50 |
| Association Structure Phase | |
| Sucrose Monooleate | 12.00 |
| Panthenol | 5.00 |
| Glycerine | 12.00 |
| Pigment | 9.00 |
| Total | 100.00 |

The ingredients for the Association Structure Phase, except for the pigments, are mixed until association structures are formed. Once the association structures are formed, the pigments are added and milled on a three roll mill. The mixture is then mixed with the other ingredients to make a homogeneous mixture. This mixture is heated to 85° C. and then poured into a mold at room temperature.

EXAMPLE II

A lipstick composition of the present invention which is substantially free of castor oil, is prepared as follows:

| Ingredient | Amount (weight percent) |
|---|---|
| Carnauba | 1.50 |
| Ozokerite | 6.00 |
| Candelillia | 4.00 |
| Hydrogenated Vegetable Oil | 5.00 |
| Isopropyl Palmitate | 11.90 |
| Isostearic Acid | 10.00 |
| Acetylated Lanolin | 4.00 |
| Propylparaben | 0.10 |
| Cetyl Ricinoleate | 10.00 |
| Ascorbyl Palmitate | 1.00 |
| Silica L-700 | 1.00 |
| Polybutene | 2.00 |
| Petrolatum | 5.50 |
| Association Structure Phase | |
| Sucrose Monooleate | 12.00 |
| Panthenol | 5.00 |
| Glycerine | 12.00 |
| Pigment | 9.00 |
| Total | 100.00 |

The composition is prepared as in Example I.

EXAMPLE III

A lipstick composition of the present invention which is substantially free of castor oil, is prepared as follows:

| Ingredient | Amount (weight percent) |
|---|---|
| Carnauba | 1.50 |
| Ozokerite | 5.50 |
| Candelillia | 4.00 |

-continued

| Ingredient | Amount (weight percent) |
|---|---|
| Hydrogenated Vegetable Oil | 5.00 |
| Acetylated Lanolin | 4.00 |
| Propylparaben | 0.10 |
| Cetyl Ricinoleate | 10.00 |
| Ascorbyl Palmitate | 1.00 |
| Polybutene | 2.00 |
| Polysiloxane Copolymer[1] | 5.97 |
| Petrolatum | 5.97 |
| Anhydrous Lanolin | 5.97 |
| Association Structure Phase | |
| Lecithin | 22.95 |
| Panthenol | 5.04 |
| Glycerine | 12.00 |
| Pigment | 9.00 |
| Total | 100.00 |

[1] #1154-141-1, supplied by GE Silicones.

The composition is prepared as in Example I.

EXAMPLE IV

A lipstick composition of the present invention is prepared as follows:

| Ingredient | Amount (weight percent) |
|---|---|
| Waxes: | |
| Ozokerite | 3.50 |
| Paraffin | 3.25 |
| Candelilla Wax | 4.65 |
| Microcrystalline Wax | 3.00 |
| Oils: | |
| Octyl Palmitate | 13.50 |
| Lanolin Oil | 8.50 |
| Isopropyl Palmitate | 8.50 |
| Maleated Soybean Oil | 2.00 |
| Cetyl Ricinoleate | 4.00 |
| Pigment Phase: | |
| Diisopropyl Dimerate | 12.00 |
| Pigment | 12.00 |
| Surfactants/Emulsifiers: | |
| Lecithin (CentrolexF) | 0.70 |
| PG-3 Diisostearate | 3.25 |
| Sorbitan Oleate | 5.00 |
| Cholesterol 12 Hydroxystearate | 2.00 |
| Dipentaerythritol Fatty Acid Ester | 4.00 |
| Polar Solvents: | |
| Glycerine | 9.00 |
| Panthenol | 1.00 |
| Miscellaneous: | |
| Tocopherol | 0.10 |
| Propylparaben | 0.05 |
| Total | 100.00 |

The pigment is slurried in the diisopropyl dimerate. The waxes and oils are placed in a beaker and melted in a steam bath at about 85° C. When the wax solids have almost melted, the mixture is mixed for twenty to thirty minutes. After mixing the beaker is removed from the steam bath and the mixture/base checked for clarity and uniformity. If some particles remain, the base should be mixed again until the particles/solids are no longer visible. The mixture is allowed to solidify. The other ingredients including the pigment slurry are mixed with a straight stainless steel spatula until uniform. The mixture is added to the base and melted over a steam bath and mixed for fifteen to twenty minutes. Once uniform, the beaker is removed and the composition poured into molds at room temperature.

EXAMPLE V

A lipstick composition of the present invention is prepared as follows:

| Ingredient | Amount (weight percent) |
| --- | --- |
| Phases A: | |
| Ozokerite | 4.45 |
| Candelilla Wax | 5.25 |
| Be Square-175 | 1.65 |
| Paraffin | 3.25 |
| Phenyl Trimethicone | 4.50 |
| Octyl Palmitate | 10.00 |
| Isopropyl Palmitate | 8.00 |
| Glyceryl Trioctanoate | 12.00 |
| Maleated Soybean Oil | 2.00 |
| Diisopropyl Dimerate | 8.00 |
| Phase B: | |
| Dipentaerythritol Fatty Acid Ester[1] | 4.50 |
| PG-3 diisostearate | 3.00 |
| Lecithin | 0.50 |
| Tocopherol Acetate | 0.05 |
| Propylparaben | 0.10 |
| Glycerine | 9.00 |
| Panthenol | 1.00 |
| Phase C: | |
| Pigment | 11.37 |
| Diisopropyl dimerate | 11.38 |
| Total | 100.00 |

[1]Cosmol 168Ar supplied by Nisshin Oil Mills, LTD.

The ingredients of Phase A are mixed together over a steam bath at about 85° C. to melt the solids. The ingredients of Phase B are mixed together and then added to Phase A which has been allowed to resolidify once a homogeneous mixture was obtained (about 20 to 30 minutes of mixing over steam bath). The mixture of Phase A and B is melted over a steam bath and mixed for about 15 to 20 minutes. The ingredients of Phase C are slurried and added to the mixture of A & B. Mix until a homogenous mixture is obtained then remove from the steam bath and pour into molds.

EXAMPLE VI

A lipstick composition of the present invention, which is substantially free of castor oil, is prepared as follows:

| Ingredient | Amount (weight percent) |
| --- | --- |
| Carnauba | 1.50 |
| Ozokerite | 5.50 |
| Candellia | 4.00 |
| Hydrogenated Vegetable Oil | 5.00 |
| Oleyl Alcohol | 5.00 |
| Isopropyl Isostearate | 7.90 |
| Acetylated Lanolin | 4.00 |
| Propylparaben | 0.10 |
| Cetyl Ricinoleate | 6.00 |
| Ascorbyl Palmitate | 1.00 |

-continued

| Ingredient | Amount (weight percent) |
| --- | --- |
| Polybutene | 2.00 |
| Association Structure Phase | |
| Lecithin | 33.00 |
| Panthenol | 5.00 |
| Glycerine | 12.00 |
| Pigment | 9.00 |
| | 100.00 |

The composition is prepared as in Example I.

EXAMPLE VII

A lipstick composition of the present invention is prepared as follows:

| Ingredient | Amount (weight percent) |
| --- | --- |
| Carnauba | 1.50 |
| Ozokerite | 5.50 |
| Candelilla | 4.00 |
| Hydrogenated Vegetable Oil | 3.00 |
| Acetylated Lanolin | 6.00 |
| Isopropyl Isostearate | 12.00 |
| Propylparaben | 0.10 |
| Oleyl Alcohol | 3.90 |
| Cetyl Ricinoleate | 7.00 |
| Ascorbyl Palmitate | 1.00 |
| Polybutene | 2.00 |
| Association Structure Phase | |
| Cetostearyl glucoside[1] | 7.20 |
| Glycerine | 12.00 |
| Panthenol | 4.80 |
| Color slurry (pigment and castor oil) | 30.00 |
| | 100.00 |

[1]Cetostearyl glucoside is a nonionic surfactant supplied as Montanol 68 Ecailles supplied by Seppic.

The waxes and oils are mixed together over a steam bath at about 85° C. until a homogeneous mixture is achieved. This base mixture is allowed to solidify. The remaining ingredients are mixed together then added to the base and placed over a steam bath (about 85° C.). The resulting mixture is mixed over the steam bath until a homogeneous mixture is achieved and then poured into molds and cooled.

EXAMPLE VIII

A lipstick composition of the present invention is prepared as follows:

| Ingredient | Amount (weight percent) |
| --- | --- |
| Carnauba | 1.50 |
| Ozokerite | 5.50 |
| Candellia | 4.00 |
| Hydrogenated Vegetable Oil | 5.00 |
| Acetylated Lanolin | 6.00 |
| Isopropyl Isostearate | 10.50 |
| Propylparaben | 0.10 |
| Oleyl alcohol | 5.40 |
| Cetyl Ricinoleate | 5.00 |
| Ascorbyl Palmitate | 1.00 |

-continued

| Ingredient | Amount (weight percent) |
| --- | --- |
| Polybutene | 2.00 |
| Association Structure Phase | |
| Schercoquat 21AP[1] | 12.00 |
| Glycerine | 12.00 |
| Color slurry: | |
| Pigment and Castor oil | 30.00 |
| | 100.00 |

[1] A cationic surfactant, Bis Isostearamidopropyl Hydroxypropyl diammonium chloride supplied by Scher Chemicals Inc.

The composition is prepared as in Example VII.

EXAMPLE IX

A lipstick composition of the present invention comprising liquid crystal association structures is prepared as follows:

| Ingredient | Amount (weight percent) |
| --- | --- |
| Carnauba | 1.50 |
| Ozokerite | 5.50 |
| Candelilia | 4.00 |
| Hydrogenated Vegetable Oil | 5.00 |
| Acetylated Lanolin | 4.00 |
| Isopropyl Isostearate | 10.50 |
| Propylparaben | 0.10 |
| Oleyl Alcohol | 3.40 |
| Cetyl Ricinoleate | 5.00 |
| Ascorbyl Palmitate | 1.00 |
| Polybutene | 2.00 |
| Liquid Crystal Phase | |
| Centrolex F* | 11.20 |
| Glycerine | 12.00 |
| Panthenol | 4.8 |
| Color Slurry | 30.00 |
| Total | 100.00 |

*(from Central Soya)

The Centrolex F, glycerine and panthenol are mixed until a liquid crystal phase (L.C.) is formed. The color slurry is a mixture of pigments (30%) slurried in castor oil (70%). The neat single phase liquid crystal is then mixed with the other ingredients to make a homogeneous mixture. This mixture is heated to 80° C. and then poured into a mold at room temperature.

EXAMPLE X

A lipstick composition of the present invention comprising liquid crystal association structures is prepared as follows:

| Ingredient | Amount (weight in grams) |
| --- | --- |
| Base | |
| Carnauba | 11.25 |
| Ozokerite | 18.00 |
| Hydrogenated Vegetable Oil | 18.00 |
| Acetylated Lanolin | 15.75 |
| Isopropyl Isostearate | 45.00 |

-continued

| Ingredient | Amount (weight in grams) |
| --- | --- |
| Propylparaben | 0.23 |
| Oleyl Alcohol | 20.25 |
| Liquid Crystal Phase | |
| Centrolex F | 18.00 |
| Glycerine | 27.00 |
| Color | |
| Castor Oil | 31.28 |
| Pigments | 20.25 |
| Total | 225.00 |

Centrolex F is an essentially oil-free lecithin powder from Central Soya (Fort Wayne, Ind.).

The lipstick is prepared as in Example IX.

EXAMPLE XI

A lipstick composition of the present invention comprising liquid crystal association structures is prepared as follows:

| Ingredient | Amount (weight percent) |
| --- | --- |
| Base | |
| Carnauba | 3.60 |
| Ozokerite | 5.76 |
| Hydrogenated Vegetable Oil | 5.76 |
| Acetylated Lanolin | 5.04 |
| Isopropyl Isostearate | 9.04 |
| Propylparaben | 0.07 |
| Oleyl Alcohol | 2.37 |
| Cetyl Ricinoleate | 10.00 |
| Liquid Crystal Phase | |
| Centrolex F (Lecithin) | 11.20 |
| Glycerine | 12.04 |
| Panthenol | 4.76 |
| Castor Oil | 21.00 |
| Pigments | 9.00 |

The panthenol is dissolved in heated glycerine and mixed with the Centrolex F to form a single phase liquid crystal. The liquid crystal is then added to remaining ingredients as in Example IX. A glossy and slippery lipstick is formed.

EXAMPLE XII

A lipstick composition of the present invention comprising liquid crystal association structures is prepared as follows:

| Ingredient | Amount (weight percent) |
| --- | --- |
| Waxes and Oils | |
| Carnauba | 3.60 |
| Ozokerite | 5.76 |
| Hydrogenated Vegetable Oil | 5.76 |
| Acetylated Lanolin | 5.04 |
| Isopropyl Isostearate | 9.40 |
| Propylparaben | 0.07 |
| Oleyl Alcohol | 2.37 |

-continued

| Ingredient | Amount (weight percent) |
|---|---|
| Silica | 5.00 |
| Cetyl Ricinoleate | 5.00 |
| Liquid Crystal Phase | |
| Centrolex F | 40.00 |
| Glycerine | 42.85 |
| Panthenol | 17.15 |
| Castor Oil | 21.00 |
| Lake | 9.00 |
| Total | 100.00 |

The lipstick is prepared as in Example XI.

Identification of Association Structures

Those skilled in the area of association structures will be able to identify association structures based upon known identification techniques.

In identifying association structures, it is preferred that the individual selected surfactants be combined with glycerine or water over a concentration range at about ambient temperature to determine if the individual selected surfactants are capable of forming association structures. When combined, surfactants and polar solvents will not form in the product if the selected surfactants do not form association structures at some concentration with glycerine or water at about ambient temperature. Well known identification techniques can be used on the mixture of the individual selected surfactants and glycerine or water.

Association structure formation for any particular surfactant and solvent combination is readily identified using one or more of several well known identification techniques. The onset of association structure formation and in particular the occurrence of the most preferred substantially one-phase liquid crystal state for a particular phosphatide or surfactant and solvent system can be identified by: (1) visual observation with the naked eye, (2) birefringent optical activity observed by light microscopy; (3) measurement of the phosphatide or surfactant/solvent system NMR spectra; (4) x-ray diffraction; (5) presence of a characteristic "texture" pattern observable under polarized light microscopy; and/or (6) texture observed in freeze fractured micrographs by transmission electron microscopy (TEM). Typically, polarized light microscopy determination requires confirmation by one of the other above mentioned methods. Light microscopy of liquid crystals is described generally in The Microscopy of Liquid Crystals, Norman, Hartshorn, London, England and Chicago, Ill., U.S.A., 1974, which discusses birefringence of mesomorphic states and methods for microscopic observation and evaluation (Chapter 1, pp. 1–20). Birefringence is a preferred method for determining the occurrence of a liquid crystal.

The identification of association structures within the lipstick product is generally more difficult due to the presence of other compounds such as wax crystals or pigments. Thus, the preferred way for identification of association structures such as liquid crystals is to ultracentrifuge the lipstick sample as previously described, separate the layers, identify the layer with typical association structure birefringence and submit that layer to testing by x-ray diffraction and/or transmission election microscopy (TEM). Freeze-fracture transmission electron microscopy (FF/TEM) is the more preferred method of identification. Most preferably, FF/TEM is utilized to confirm association structures which have been indicated by other well-known methods such as x-ray diffraction or NMR.

A preferred method for determining the occurrence of the association structures of the present invention is by transmission election microscopy (TEM). More preferably, the association structures are imaged by a freeze-fracture transmission electron microscopy (FF/TEM) method. The method is carried out as follows:

1. The outside cavity of a freezing container is filled with liquid nitrogen and the inner dewar of the freezing container is filled with liquid ethane (normal melting temperature of −172° C.). The ethane is allowed to freeze.
2. A small piece (1 mm×2 mm) is cut from the lipstick with a clean razor blade and placed in the well of a copper specimen holder.
3. Most of the frozen ethane in the dewar is melted by inserting a metal heat sink into the dewar.
4. Immediately after melting the ethane, the specimen holder containing the lipstick sample is picked up using a pair of tweezers and rapidly plunged into the liquid ethane.
5. After a few seconds, the specimen holder is removed from the ethane, quickly touched to the tip of a camel's hair brush to remove excess ethane, and immediately immersed in the liquid nitrogen to keep the sample cold.
6. The sample is transferred under liquid nitrogen to a JEOL JFD-9000C sample holder and then transferred into the chamber of a JEOL JFD-9000C freeze fracture unit. The temperature of the specimen stage in the unit should be about −175° C. Vacuum should be at least $5\times10^{-7}$ torr.
7. A knife inside the unit is cooled to a temperature of about −165° C.
8. The sample is fractured in the JEOL chamber using the pre-cooled knife.
9. Platinum-carbon is deposited onto the fractured sample at a 45° angle for 4.5 seconds, followed by carbon deposition at a 90° angle for 25 seconds to form a replica of the fractured sample. The high voltage is 2500 V and the current is 70 mA.
10. The samples are removed from the freeze-fracture unit and cleaned in subsequent solutions of warm Dawn® (a liquid dishwashing detergent sold by The Procter and Gamble Company) in water, methanol, chloroform/methanol, and chloroform to remove the sample from the replica.
11. The replicas are picked up on 300 mesh copper EM grids and examined in a transmission electron microscope.
12. Images are recorded on negative film and positive prints are made from the negatives.
13. The prints are then examined by one of ordinary skill in the art for identification based upon known identification techniques.

The freeze-fracture transmission electron microscopy method is descibed generally in the following references which are incorporated herein by reference: Rash, J. E. and Hudson, C. S., *Freeze-Fracture: Methods, Artifacts and Interpretations*, New Haven Press, New York, 1979; and Steinbrect and Zierold, *Cryotechniques in Biological Electron Microscopy*, Springer-Verlag, Berlin, 1987. The use of the freeze-fracture transmission electron microscopy method for structure determination and identification is generally described in the following references which are incorporated herein by reference: Gulik-Krzywicki, T., Aggerbeck, L. P. and Larsson, K., "The use of Freeze-Fracture and Freeze-Etching Electron Microscopy for Phase Analysis and Structure Determination of Lipid Systems," *Surfactants in Solution*, K. L. Mittal and B. Lindman, eds., Plenum Press, New York, pp. 237–257, 1984; and Zasadzinski, J. A. N. and Bailey, S. M., "Applications of Freeze-Fracture Replication to Problems in Materials and Colloid Science," J. Elect. Micros. Tech., 13:309–334, 1989.

What is claimed is:

1. A lipstick composition comprising:
   (a) from about 5% to about 90%, by weight, wax;
   (b) from about 1% to about 90%, by weight, of an emollient component comprising from 0% to about 100%, by weight, of oil liquid at ambient temperature;
   (c) from about 0.1% to about 80%, by weight, of an association structure consisting essentially of:
       (1) from about 3% to about 96%, by weight, of polar solvent; and
       (2) from about 4% to about 97%, by weight, of surfactant having a Krafft point at or below about ambient temperature;
   (d) from about 0% to about 35%, on an anhydrous basis, color.

2. A lipstick composition according to claim 1 wherein said surfactant is selected from the group consisting of amphoteric surfactants, anionic surfactants, cationic surfactants, nonionic surfactants and mixtures thereof.

3. A lipstick composition according to claim 2 wherein said association structure is selected from the group consisting of reverse micelles, lyotropic liquid crystals and mixtures thereof.

4. A lipstick composition according to claim 3 wherein said association structure is selected from the group consisting of cylindrical reverse micelles, reverse hexagonal liquid crystals, cubic liquid crystals, lamellar liquid crystals and mixtures thereof.

5. A lipstick composition according to claim 4 wherein said association structure is selected from the group consisting of lamellar liquid crystals, reverse hexagonal liquid crystals and mixtures thereof.

6. A lipstick composition according to claim 3 wherein said reverse micelles aggregate to form networking spherical structures, elongated structures cylindrical structures, filament structures or mixtures thereof.

7. A lipstick composition according to claim 5 wherein said lamellar liquid crystals are substantially one phase.

8. A lipstick composition according to claim 2 wherein said association structure comprises from about 3% to about 75% of the lipstick composition.

9. A lipstick composition according to claim 8 wherein said association structure comprises from about 10% to about 65% of the lipstick composition.

10. A lipstick composition according to claim 8 wherein said polar solvent comprises from about 10% to about 80% of the association structure and wherein said surfactant comprises from about 30% to about 80% of the association structure.

11. A lipstick composition according to claim 3 wherein said polar solvent is selected from the group consisting of water, glycerine, propylene glycol, butyleneglycol, panthenol and mixtures thereof.

12. A lipstick composition according to claim 11 wherein said polar solvent is selected from the group consisting of glycerine, propylene glycol, panthenol, butyleneglycol, and mixtures thereof.

13. A lipstick composition according to claim 3 wherein said surfactant is selected from the group consisting of amphoteric surfactants, cationic surfactants, nonionic surfactants and mixtures thereof.

14. A lipstick composition according to claim 13 wherein said surfactant is selected from the group consisting of nonionic surfactants.

15. A lipstick composition according to claim 2 wherein said lipstick composition is substantially free of castor oil.

16. A lipstick composition according to claim 12 wherein said lipstick composition is substantially free of water.

17. A lipstick composition according to claim 8 wherein said emollient component comprise from about 10% to about 80% of the lipstick composition.

18. A lipstick composition according to claim 17 wherein said oil comprises from about 5% to about 90% of the emollient component.

19. A lipstick composition according to claim 18 wherein said oil is selected such that at least about 75% of the types of oils used have solubility parameters which do not differ by more than from about 0.3 to about 1.

20. A lipstick composition according to claim 19 wherein said oil is selected such that at least about 99% of the types of oils used have solubility parameters which do not differ by more than from about 0.5 to about 0.8.

21. A lipstick composition according to claim 8 wherein said wax comprises from about 10% to about 30% of the lipstick composition.

22. A lipstick composition according to claim 21 wherein said wax is selected from the group consisting of:
   candelilla,
   beeswax,
   carnauba,
   spermaceti,
   montun,
   ozokerite,
   ceresin,
   paraffin,
   modified beeswax,
   bayberry,
   castor waxes,
   synthetic waxes,
   microcrystalline waxes, and mixtures thereof.

23. A lipstick composition according to claim 22 wherein said wax is selected from the group consisting of microcrystalline waxes, candelilla, modified beeswax, ozokerite, paraffin and mixtures thereof.

24. A lipstick composition according to claim 23 wherein said lipstick composition comprises from about 3% to about 6% candelilla wax, from about 2% to about 5% ozokerite wax, from about 2% to about 5% paraffin wax, and from about 1% to about 4% microcrystalline wax.

25. A lipstick composition according to claim 9 wherein said color comprises from about 1% to about 20% of the lipstick composition.

26. A lipstick composition according to claim 25 wherein said lipstick composition is substantially free of lecithin.

27. A lipstick composition according to claim 2 further comprising from about 1% to about 10% of a coupling agent.

28. A lipstick composition according to claim 27 wherein said polar solvent is present in the lipstick composition at a level of from about 0.1% to about 30% and said surfactant is present in the lipstick composition at a level of from about 5% to about 20%.

29. A lipstick composition according to claim 28 wherein said surfactant is a mixture having from about 50% to about 75% of the mixture being surfactants which have a Krafft point at or below about ambient temperature and form association structures at ambient temperature and from about 25% to about 50% of the mixture being surfactants which are coupling agents.

30. A process for incorporating dry pigments into a lipstick composition containing association structures comprising the steps of:
   (a) preparing a mixture of association structures consisting essentially of:
       (1) a polar solvent;
       (2) a surfactant selected from the group consisting of amphoteric surfactants, cationic surfactants, anionic surfactants, nonionic surfactants having a Krafft point at or below about ambient temperature and mixtures thereof;

(b) stirring said mixture until uniform;
(c) adding dry pigments to said mixture with mixing until achieving a homogeneous mixture;
(d) milling said mixture until uniform particle size is achieved; and
(e) adding said mixture to the remaining lipstick ingredients with mixing until a homogeneous mixture is achieved.

31. A lipstick composition comprising:
(a) from about 0.1% to about 30% polar solvent;
(b) from about 5% to about 20% of a surfactant mixture consisting essentially of lecithin, PG-3 diisosterate, sorbitan oleate, cholesterol 12 hydroxystegrate, and dipentaerythritol fatty acid ester.

* * * * *

UNITED STATES PATENT AND TRADEMARK OFFICE
CERTIFICATE OF CORRECTION

PATENT NO.    : 6,325,995 B1              Page 1 of 1
DATED         : December 4, 2001
INVENTOR(S)   : Magda El-Nokaly et al.

It is certified that error appears in the above-identified patent and that said Letters Patent is hereby corrected as shown below:

Tite page,
Item [54], "LIPSTICKS" should read -- LIPSTICK --.

Column 7,
Line 40, "T122" should read -- T101 --.

Column 15,
Lines 15-16, "Blue I Aluminum" should read -- Blue 1 Aluminum --.

Column 26, lines 57 to Column 27, line 8,
Claim 30 should be deleted.

Signed and Sealed this

Twenty-fourth Day of December, 2002

JAMES E. ROGAN
*Director of the United States Patent and Trademark Office*